(12) United States Patent
Gare

(10) Patent No.: US 7,182,968 B2
(45) Date of Patent: Feb. 27, 2007

(54) COMPOSITION CONTAINING XYLITOL AND FIBER

(76) Inventor: Fran Gare, 220 E. 57 St., New York, NY (US) 10022

( * ) Notice: Subject to any disclaimer, the term of this patent is extended or adjusted under 35 U.S.C. 154(b) by 0 days.

(21) Appl. No.: 09/759,567

(22) Filed: Jan. 11, 2001

(65) Prior Publication Data

US 2002/0127319 A1    Sep. 12, 2002

(51) Int. Cl.
*A23L 1/236* (2006.01)
(52) U.S. Cl. ............... 426/548; 426/74; 426/549; 426/580; 426/583
(58) Field of Classification Search ............... 426/548, 426/655, 74, 549, 580, 583
See application file for complete search history.

(56) References Cited

U.S. PATENT DOCUMENTS

| | | | |
|---|---|---|---|
| 3,876,794 A | | 4/1975 | Rennhard .................. 426/152 |
| 4,379,782 A | * | 4/1983 | Staub et al. ............... 424/180 |
| 4,442,132 A | * | 4/1984 | Kim ........................... 426/549 |
| 4,514,422 A | | 4/1985 | Yang et al. ................... 426/3 |
| 4,834,990 A | | 5/1989 | Amer ........................ 426/74 |
| 4,950,140 A | * | 8/1990 | Pflaumer et al. ............ 424/439 |
| 4,952,413 A | | 8/1990 | LaBarge et al. .............. 426/6 |
| 5,098,730 A | * | 3/1992 | Pepper et al. .............. 426/548 |
| 5,223,303 A | | 6/1993 | Taskinen ................... 426/660 |
| 5,422,127 A | * | 6/1995 | Dube et al. |
| 5,468,509 A | | 11/1995 | Schlup et al. .............. 426/548 |
| 5,681,606 A | | 10/1997 | Hutchison et al. ......... 426/590 |
| 5,711,982 A | * | 1/1998 | Takemori et al. |
| 5,871,798 A | | 2/1999 | Hutchison et al. ......... 426/590 |
| 6,056,984 A | | 5/2000 | Ekanayake et al. ......... 426/120 |
| 6,827,955 B2 | * | 12/2004 | McCabe ...................... 426/89 |
| 6,830,766 B2 | * | 12/2004 | McCabe ...................... 426/89 |

OTHER PUBLICATIONS

Kuntz, L.A., Food Product Design, Bulking Agents: Bulking Up While Scaling Down, Jun. 1996, from www.foodproductdesign.com/archive/1996/0696CS.*
Sugarsure product, from www.arnoldlabs.com/html/sugarsure.*
Muscle Optimeal—The Ultimate Diet Meal, from www.prolithic.com/hpages/efoods/optimeal.*

* cited by examiner

*Primary Examiner*—Leslie Wong
(74) *Attorney, Agent, or Firm*—Keusey, Tutunjian & Bitetto, P.C.

(57) ABSTRACT

A composition containing psyllium fiber and xylitol. The composition is in one of powered, liquid or product form. In powdered form the composition is used for producing confectionery products, beverages, baked good products, bakery products, snack bars and similar foodstuff products. In product form, the composition is used to produce confectionery products, baked good products, bakery products, snack bars and similar foodstuff products. The fiber is preferably psyllium fiber. However, the psyllium fiber may be substituted with fruit fiber and derivatives including pectin; seaweed gums and derivatives, including carrageenan, agar and alginates; cellulose and derivatives; cereal grain fibers, including corn, wheat, oat, rice, barley and soy; fructooligosaccharides and its derivatives; seed gums, including guar and locust bean; tree gums, including karaya, tragacanth and acacia; xantham gum; vegetable fiber, including pea and legumes; and potato fiber. Suitable natural flavorings, which can be added to the composition containing xylitol and fiber include but are not limited to all nuts, all green vegetables and legumes, carrots, chocolate, cocoa, vanilla, orange, lemon, lime, grapefruit, peach, apricot, nectarine, strawberry, blueberry, raspberry, peppermint, coffee, cinnamon, mocha, tomato, herbs (green tea, ginger, ginseng, etc.) and the like.

18 Claims, No Drawings

COMPOSITION CONTAINING XYLITOL AND FIBER

BACKGROUND OF THE INVENTION

1. Field of the Invention

The present invention relates generally to compositions containing reduced calories, reduced carbohydrates and sugar substitutes and, more particularly, to a composition containing xylitol and fiber in a powdered, liquid and/or product form.

2. Description of the Prior Art

A variety of food and drink products as well as powdered mixes are presently available which contain both fats and sugars. For example, chocolate-flavored confectionery products comprise cocoa butter or a cocoa butter fat substitute, and sugar, typically in the form of sucrose. Other examples of such products are baked goods such as cookies, brownies and cakes and frozen desserts such as ice cream. Numerous beverages and powdered mixes for use in producing foodstuffs and beverages also contain fattening amounts of sugar.

The fat and sugar components in such products can provide a significant number of calories. In the case of fat, the caloric load is due to the triglycerides that are present. For example, a natural fat, such as corn oil, provides a caloric density of about 9 calories per gram. By comparison, vegetable protein provides only about 4 calories per gram.

A number of solutions have been proposed for replacing the fat component in such products. For example, gums and other thickeners are typically used to replace a portion of the fat component by increasing the amount of water that is present. However, these substitutes often have a number of undesirable properties, particularly in the textural and flavor area. Accordingly, it would be desirable to provide a substitute for higher calorie fats other materials which have reduced calories while maintaining the textural and flavor properties of fat.

In the case of sugars, sucrose is often used in such products, particularly in drinks. It is well known that sucrose imparts a significant number of calories to such food products. The caloric density of sucrose is about 4 calories per gram. In addition, certain diseases, in particular diabetes, require the affected person to restrict their intake of sucrose and other sugars.

A variety of high intensity, reduced calorie sweeteners have been developed to replace sugar. Prominent examples of such reduced calorie sweeteners are aspartame and acesulfame. While these materials can replace the sweetness component, they are totally incapable of providing the other functional properties of sugar. These other functional properties include water activity ($a_w$) reduction, control of starch gelatinization temperature, and viscosity.

A variety of bulking or bodying agents have been proposed to replace sugars to provide these other functional properties. These bulking agents include cellulosic derivatives such as carboxymethylcellulose, hydrocolloid gums and certain wholly or partially nondigestible carbohydrates. A prominent example of such partially nondigestible carbohydrates is the polyglucose derivative referred to as polydextrose. U.S. Pat. Nos. 3,876,794 and 3,766,165 to Rennhard, issued Apr. 8, 1975 and Oct. 16, 1973, respectively, disclose the use of polydextrose and its related polyglucose derivatives as non-nutritive carbohydrate substitutes in a variety of food products including cakes, dietetic ice cream, low calorie salad dressings, chocolate coating formulations, whipped toppings and French salad dressings.

Polydextrose does not behave like a simple sugar and particularly does not have the same baking properties as sugars. Instead, it functions more as a filler or viscosity controlling agent, much like starch dextrins. Polydextrose works very well in low water systems such as hard candies. However, in intermediate water containing baked goods systems, such as brownies and cookies, polydextrose does not work very well. Polydextrose can also be used in high water systems such as cakes and ice creams, but requires strict formulation control. Accordingly, it would be desirable to have a reduced calorie substitute for sugar that provides its functional properties in a variety of food products and drinks without requiring strict formulation control.

Numerous prior art disclosures are directed to the use of sugar substitutes in foods. The U.S. patents listed and described below all are illustrative of such prior art.

U.S. Pat. No. 6,056,984

Inventor: Ekanayake

Issued: May 2, 2000

Shelf-stable complete pre-mixes, separated into two or more components. The components are chemically and microbially stable. At least one component is a high-water-activity liquid component having a pH greater than 4.5. The components, when combined, provide all ingredients necessary to form uncooked mixes or food and beverage products.

U.S. Pat. No. 6,045,850

Inventor: Kondou

Issued: Apr. 4, 2000

A low-calorie compounded cocoa composition comprising cocoa powder, erythritol, and a sweetener of high sweetness (e.g., Stevia and Aspartame). It is lower in calories than conventional compounded cocoa composition containing sucrose as a sweetener and is pleasant to the taste.

U.S. Pat. No. 5,871,798

Inventor: Hutchison et. al.

Issued: Feb. 16, 1999

A method is disclosed of preparing a beverage in the form of a dilute aqueous solution, suspension or dispersion of an encapsulated product. The capsule is added to a potable liquid, and the capsule material breaks down when submerged in the liquid to release its contents and itself dissolve. A primary advantage of providing the product in this way is that it can be confined within the capsule in liquid form, and can therefore disperse or dissolve in water more readily. Additionally, the capsule would normally sink to the bottom of the body of water before releasing its contents, thereby ensuring that the contents are released within the body of water, and not at the surface thereof.

U.S. Pat. No. 5,681,606

Inventor: Hutchison et. al.

Issued: Oct. 28, 1997

A method is disclosed of preparing a beverage in the form of a dilute aqueous solution, suspension or dispersion of an encapsulated product. The capsule is added to a potable liquid, and the capsule material breaks down when submerged in the liquid to release its contents and itself dissolve. A primary advantage of providing the product in this way is that it can be confined within the capsule in liquid form, and can therefore disperse or dissolve in water more readily. Additionally, the capsule would normally sink to the bottom of the body of water before releasing its contents, thereby ensuring that the contents are released within the body of water, and not at the surface thereof.

U.S. Pat. No. 5,468,509

Inventor: Schlup et. al.

Issued: Nov. 21, 1995

A product and process is provided to produce a one phase chocolate tablet containing from 1 to 16 percent water eliminating the normally required conching step.

U.S. Pat. No. 5,223,303

Inventor: Taskinen

Issued: Jun. 29, 1993

Crystalline xylitol is added to a melt containing xylitol and other sugar alcohols, such as maltitol, lactitol, and hydrogenated glucose syrup. By careful control of temperature and the amounts of crystalline xylitol added to the molten mixture, hard candies with low tack and good dimensional stability result.

U.S. Pat. No. 4,952,413

Inventor: LaBarge et. al

Issued: Aug. 28, 1990

Food compositions are substantially sugar or fat-free, comprise a texturizing amount of a polyalkylene oxide polymeric composition, and have a texture substantially similar to food compositions containing sugar or fat.

U.S. Pat. No. 4,834,990

Inventor: Amer

Issued: May 30, 1989

An improved non-dairy liquid food product is made by adding dietary fiber and calcium to a fruit juice or a drink. The dietary fiber may include soluble, insoluble dietary fiber or mixtures there of. Any soluble, insoluble, organic or inorganic calcium salt may be employed.

U.S. Pat. No. 4,514,422

Inventor: Yang et. al.

Issued: Apr. 30, 1985

The present invention relates to a gum composition exhibiting improved shelf life and resistance to staling, that comprises a substantially anhydrous mixture of a gum base, at least one sugar alcohol, and glycerin, the glycerin present in an amount ranging from greater than 10% to about 18% by weight of the composition. The gum composition preferably contains no more than 2% by weight of water. The invention includes a method for preparing the gum composition, comprising treating the ingredients thereof, including the glycerin, to remove substantially all water therefrom, thereafter combining the sugar alcohol with the glycerin under agitation and at about 50 deg. C., and adding subsequently thereto the gum base, after which certain additive materials, such as flavorings are added, and the like may be added with mixing.

U.S. Pat. No. 4,442,132

Inventor: Kim

Issued: Apr. 10, 1984

The products contain less than 10% by weight of digestible carbohydrate and are prepared in the conventional way from dough or batter comprising egg in the form of whole egg or egg albumin, 2–30% by weight of flour substitute such as calcium caseinate, sodium caseinate, ammonium caseinate, acid caseinate, soy protein and the like, of which at least 50% by weight is supplied by calcium caseinate, 15% wheat flour which is present in an amount less than the amount of flour substitute, 3–40% by weight of minced nuts, 5–50% by weight of sugar alcohol selected from lactitol, sorbitol, and xylitol, and 0% by weight of sugar. The use of lactitol as the sugar alcohol provides crispy products which maintain their crispness for several months when protected from moisture.

U.S. Pat. No. 3,876,794

Inventor: Rennhard

Issued: Apr. 8, 1975

Non-nutritive carbohydrate substitutes are prepared by polycondensation of saccharides in the presence of polycarboxylic acid catalyst at reduced pressure and are useful in dietetic food compositions.

While these references may be suitable for the particular purpose to which they address, they would not be as suitable for the purposes of the present invention as heretofore described.

It is thus desirable to provide a composition containing Xylitol and fiber which is able to overcome the deficiencies of the prior art by maintaining the flavor and texture of products containing sugar and fat. It is further desirable to provide a composition containing Xylitol and fiber in a powdered, liquid concentrate, liquid beverage or solid product form. It is still further desirable to provide a composition containing Xylitol and fiber with additional flavorings based upon the desired tastes of the end user. It is even further desirable to provide a composition containing Xylitol and fiber wherein the powdered form may be used to produce any of bakery, snack products and beverages. It is yet further desirable to provide a composition containing Xylitol and fiber produced in a product form of at least any one of a snack bar, bakery products and beverages. It is still further desirable to provide a composition containing Xylitol and fiber wherein the product form further includes blending salt, sucralose, calcium sodium caseinate and whey protein concentrate. It is even further desirable to provide a composition containing Xylitol and fiber wherein the fiber is at least one of psyllium fiber, fruit fiber and derivatives including Pectin, seaweed gums and derivatives, including carrageenan, agar and alginates, cellulose and derivatives, cereal grain fibers, including corn, wheat, oat, rice, barley and soy, fructooligosaccharides and its derivatives, seed gums, including guar and locust bean, tree gums, including karaya, tragacanth and acacia, xantham gum, vegetable fiber, including pea and legumes and potato fiber.

SUMMARY OF THE PRESENT INVENTION

The present invention relates generally to compositions containing reduced calories, reduced carbohydrates, and sugar substitutes and, more particularly, to a composition containing fiber and xylitol in a powdered, liquid and/or product form.

A primary object of the present invention is to provide a composition containing xylitol for use in food products that will overcome the shortcomings of prior art foodstuffs containing sugar and/or sugar substitutes.

A further object of the present invention is to provide a composition containing xylitol and fiber in the form of a powdered, liquid, liquid concentrate and/or mix for producing beverages, dairy desserts, snack products, toppings, bakery products, salad dressing, chocolate and other soft candies that will overcome the shortcomings of prior art mixes containing sugar and/or sugar substitutes.

A yet further object of the present invention is to provide composition containing xylitol and fiber and further including natural flavorings from the addition of low carbohydrate, natural foodstuffs to the composition.

Another object of the present invention is to provide composition containing xylitol and fiber wherein additional flavor is provided by the addition of vegetables, fruits, nuts, herbs and other flavorings to the composition.

A further object of the present invention is to provide a composition containing xylitol and fiber for use in candy and snack bars that will overcome the shortcomings of sugar containing prior art candy and snack bars.

A still further object of the invention is to provide a composition containing xylitol and fiber containing no sugar and yet flavorful which can be used in producing numerous foodstuffs or beverages.

The present invention relates to a composition containing xylitol and fiber which can be added to a variety of previously fat-containing and sugar-containing foodstuffs which comprises herein disclosed amounts of xylitol and fiber. The composition may also contain blending salt; sucralose flavorings; Calcium Sodium Caseinate; and Whey Protein Concentrate. The fiber used is preferably Psyllium fiber. However, psyllium fiber can be substituted for with numerous other fibers listed below in this application. Additionally, a variety of low carbohydrate flavorings are added from natural fruits, vegetables, nuts and herbs as disclosed herein.

According to the present invention it has, however, turned out that by the use of the ingredients defined below, which are all natural food ingredients, in the proportions specified, it is possible to obtain reduced calorie products that fulfil the conditions specified above for even diabetics, which makes it suitable as an isocaloric substitute for foods and beverages in insulin resistant, weight loss and yeast-free diabetic diets. Furthermore, it has turned out that consumption of various food products and beverages using the herein disclosed composition by diabetics yields a surprisingly efficient and protracted reduction of blood sugar concentration.

To the accomplishment of the above and related objects, this invention will be described in further detail and the preferred embodiments described may be modified by one skilled in the art but will still be within the scope of the appended claims.

DETAILED DESCRIPTION OF A PREFERRED EMBODIMENT

The composition containing fiber, gum and xylitol of the present invention will now be described in greater detail. The composition containing fiber, gum and xylitol may be in the form of a powder or liquid for producing a variety of foodstuffs and beverages as well as combined in product form such as by not limited to snack bars, candies, bakery products, dairy desserts, dairy products, toppings and salad dressings.

A preferred embodiment of the no sugar, low carbohydrate, low-calorie composition of the present invention contains xylitol and fiber as the major ingredients. The embodiment provided below in Example 1 also includes blending salt, sucralose, calcium sodium caseinate and whey protein concentrate. The fiber used in this example is psyllium fiber. However, the psyllium fiber may be substituted for with at least any one of fruit fiber and derivatives including pectin, seaweed gums and derivatives, including carrageenan, agar and alginates, cellulose and derivatives, cereal grain fibers, including corn, wheat, oat, rice, barley and soy, fructooligosaccharides and its derivatives, seed gums including guar and locust bean, tree gums, including karaya, tragacanth and acacia, xantham gum, vegetable fiber including peas and legumes and potato fiber.

Cocoa powder is added to the embodiment to provide additional flavoring, in this instance, a chocolate flavor. The cocoa powder may be substituted for by any low carbohydrate flavoring including but not limited to all nuts, all green vegetables, carrots, tomatoes, fruits including all berries and melons and herbs. The flavoring may comprise 0.1–75.0% by weight of the composition. For preparing, as an example, a chocolate cake baking mix, the composition Xylitol, gum and fiber of the present invention described above, is mixed together in the following preferred percent weight ranges:

EXAMPLE 1

| Ingredient | Percent (%) Wt. Range |
| --- | --- |
| Xylitol | 5–99 |
| Salt (blending) | 0.1–4.0 |
| Sucralose | 0.001–1.0 |
| Cocoa Powder | 10–60.0 |
| Calcium Sodium Caseinate | 0.1–15.0 |
| Whey Protein Concentrate | 0.1–40.0 |
| Psyllium fiber | 0.1–25.0 |

When preparing a liquid concentrate or beverage, xylitol is used in a weight percentage of 0.1–95%.

An Example of serving sizes for the chocolate baking mix, by way of ingredient units (units are in grams), Chart 1 is followed:

CHART 1

| Ingredient | 1 Serving | 100 unit | Final Batch |
|---|---|---|---|
| Xylitol | 121.8800 | 47.9095 | 479.0954 |
| Salt (blending) | 1.4000 | 0.5503 | 5.5032 |
| Sucralose | 0.1161 | 0.0456 | 0.4564 |
| Cocoa Powder | 80.0000 | 31.4470 | 314.4702 |
| Calcium Sodium Caseinate | 9.0000 | 3.5378 | 35.3779 |
| Whey Protein Concentrate | 37.0000 | 14.5442 | 145.4425 |
| Psyllium fiber | 5.000 | 1.9654 | 19.6544 |
| TOTAL | 254.3961 | 100.0000 | 1000.0000 |

When preparing a beverage using water, the composition should compose substantially 80% water. Beverages formed with liquids other than water will include amounts of the liquid as disclosed hereinafter.

A preferred method for preparing the composition containing xylitol and fiber of the present invention listed above is as follows:

The xylitol and blending salt are sifted through a 10 mesh screen into a mixing machine and mixed for substantially 2 minutes. With the mixing machine still running, the sucralose, cocoa powder, calcium sodium caseinate, whey protein concentrate and the psyllium fiber are sifted though an 18 mesh screen into the mixing machine with the sifted and mixed xylitol and blending salt and mixed for an additional substantially 3–4 minutes. The composition containing xylitol and fiber is now ready for use in either powdered form of for production of any foodstuff.

The psyllium fiber can also be substituted with any of the fibers listed below:
1) Fruit Fiber and derivatives including Pectin;
2) Seaweed Gums and derivatives, including Carrageenan, Agar and Alginates;
3) Cellulose and derivatives;
4) Cereal Grain Fibers, including Corn, Wheat, Oat, Rice, Barley and Soy;
5) Fructooligosaccharides and its derivatives;
6) Seed Gums, including Guar and Locust Bean;
7) Tree Gums, including Karaya, Tragacanth and Acacia;
8) Xantham Gum;
9) Vegetable Fiber, including Pea and Legumes;
10) Potato Fiber;
11) Water, Distilled, D1, R0 or mineral.

When preparing foodstuffs with the composition containing xylitol and fiber of the present invention, conventional procedures are followed based upon the recipe for preparation of the foodstuff. The composition containing xylitol and fiber is mixed in with the other ingredients of the foodstuff while obviating the need to add sugars and sugar substitutes in accordance with the recipe.

As far as mixing the powdered form of the composition containing xylitol and fiber to form foodstuffs and beverages, various modifications can be made without departing from the spirit of the invention. Typically, when preparing a beverage, the fruit juice, drink or other liquid food used to form the beverage will contain up to 10% by weight of dietary fiber of which 0–100% could be of the soluble variety. It could desirably also contain about 100–2000 mg., and preferably about 300 to 1,000 mg., of elemental calcium per 8 oz. serving in the form of one or a mixture of suitable calcium salts. The selection of the specific calcium salt or mixture of such salts is determined primarily by the desired properties of the fruit juice, drink or other liquid food as regards pH, taste characteristics, clarity characteristics, cost and the desired elemental calcium content.

Besides calcium sodium caseinate, any non-toxic soluble, insoluble, organic or inorganic calcium salt or salts may be employed, such as calcium lactate, calcium chloride, calcium oxide, calcium sulphate, calcium citrate, calcium ascorbate, calcium acetate, calcium gluconate, monocalcium phosphate, dicalcium phosphate, tricalcium phosphate, calcium tartarate, etc.

Examples of water-insoluble dietary fiber which may be used in the composition of the present invention include natural cereal, fruit, grain, celluloses and modified celluloses, such as methyl cellulose, hydroxyethyl cellulose, hydroxypyropyl cellulose, carboxymethyl cellulose and other similar modified celluloses.

Examples of water-soluble dietary fiber which may be used in the composition of the present invention include plant gums and plant derivatives such as gum arabic, locust bean gum, citrus pectins, low and high methoxy pectin, gum tragacanth, agar, carrageenan, xanthan gum, guar gum, alginic acid salts, gum ghatti, Irish moss, gum karia and the like. Mixtures of soluble and insoluble dietary fiber may also be employed.

It is an important feature or embodiment of this invention that to ensure a stable suspension of any insoluble dietary fiber and insoluble calcium salts in about 0.1 to about 0.5 wt. % of a stabilizer mixture containing carboxymethyl cellulose (15–45%), guar gum (15–45%), locust bean gum (15–30%) and carrageenan (12.5–22.5%) is desirably used in proportion to the amount of insoluble material. Typically, the weight ratio of stabilizer: insoluble fiber and/or calcium may range from about 0.1:1 to about 1:1, preferably about 0.2:1 to about 0.5:1, but amounts of stabilizer over about 0.5–0.6 wt. % in the product tend to unduly thicken or increase the viscosity of the product and are hence preferably avoided.

In preparing the powdered form of the composition containing xylitol and fiber for combination with juices, drinks or other non-dairy drinkables having strong taste and color, it is possible to use salts of calcium that have acid tastes such as calcium chloride and calcium monophosphate without significant taste impact may be used. In cloudy juices, drinks and other drinkable liquids insoluble calcium salts, which are usually less expensive, such as calcium carbonate, calcium sulphate, calcium triphosphate, and use the stabilizer system to produce a stable suspension may be used.

The above-described dietary fiber and calcium salts are conveniently added to a drinkable aqueous liquid food product such as soups, carbonated or non-carbonated natural or artificial drinks, vegetable juices, and preferably natural fruit drinks and juices such as peach, nectarine, orange, pineapple, grape, grapefruit, lemon, lime, blueberry, strawberry, raspberry, apple juices and drinks. Such liquid food products generally contain the characteristic fruit or other solute dissolved in water which normally constitutes at least about 50%, generally at least 70% up to about 97–98% of the liquid.

The liquid food products of this invention may contain from about 0.001 to about 1% of any desired flavor and/or sweetener. Suitable natural flavors, which can be added to the composition containing xylitol and fiber include flavorings are added from all nuts, all green vegetables and legumes, carrots, chocolate, cocoa, vanilla, orange, lemon, lime, grapefruit, peach, apricot, nectarine, strawberry, blueberry, raspberry, peppermint, coffee, cinnamon, mocha, tomato, herbs (green tea, ginger, ginseng, etc.) and the like.

A suitable method for preparing a liquid food product of this invention comprises mixing the dietary fiber and the preferred calcium salts and stabilizer system with a fraction (about 15–25%) of the total fruit juice or other aqueous liquid food until completely dispersed and soluble components dissolved. The finished liquid product will preferably comprise substantially 2%–5% solids. In some cases, heating may be desirable or essential to complete this step, e.g. at least up to about 180° C. for 1 to 3 minutes. The resulting mixture is then thoroughly dispersed into the remainder of the total fruit juice and the xylitol composition of this invention using said mixing blender till homogeneous. The final mixture is then bottled, canned or boxed and sterilized in the usual way While the invention has been described in detail and with reference to specific examples thereof, it will be apparent to one skilled in the art that various changes and modifications can be made therein without departing from the spirit and scope thereof.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A food composition for providing natural sweetening, bulking properties, binding, stabilization, texture and support without artificial sweeteners, gluten and sugar for use in a recipe to produce a sugar-free food product, the food composition comprising:
   a gluten-free baked product mix including:
   a sugarless natural sweetening agent having particular functional properties of sugar, said sweetening agent comprising xylitol;
   a whey protein in an amount between about 2 to about 40% by weight to support a structure of the food product produced using the food composition; and
   at least one of a fiber or a stabilizer, said fiber to provide water-binding capacity and to provide additional bulk without adding caloric value, wherein the mix provides a baked product having consistency and texture equivalent to conventional baked products without the use of gluten.

2. The food composition of claim 1, wherein the fiber comprises a mixture of soluble and insoluble fibers.

3. The food composition of claim 1, wherein the stabilizer comprises about 0.1 to about 0.5% by weight of the food composition.

4. The food composition of claim 2, further comprising at least one of a non-toxic soluble or insoluble calcium salt.

5. The food composition of claim 4, wherein a weight ratio of the stabilizer to the insoluble fiber and an insoluble non-toxic calcium salt is about 0.1:1.0 to about 1.0:1.0.

6. The food composition of claim 1, wherein particular functional properties comprise water activity reduction, control of starch gelatinization, heat stability, bulking capability and viscosity.

7. The food composition of claim 1, wherein the food product is included in at least one of a dairy product, a snack bar, a salad dressing, a candy, a topping and a beverage.

8. The food composition of claim 1, wherein said xylitol is provided in amounts able to sweeten the composition to a desired level and provide bulking capability, said bulldng agent is provided in amounts able to provide water-binding capacity thereby increasing the viscosity of the preparation to a desired level and providing additional bulk without adding caloric value, and said stabilizer is provided in amounts able to provide a desired amount of elasticity and binding to foodstuffs produced using said composition.

9. A dietetic food composition free of artificial sweeteners, gluten and sugar for use in a recipe to prepare a sugar-free foodstuff, the food composition comprising:
   a gluten-free baked product mix for baked goods or snacks bars including:
   a sugarless natural sweetening agent having particular functional properties of sugar, said sweetening agent comprising xylitol;
   a whey protein in an amount between about 2 to about 40% by weight to support a structure of the food product produced using the food composition;
   a non-toxic soluble or insoluble calcium salt;
   a low carbohydrate flavoring; and
   at least one of a bulking agent comprising at least one fiber to provide water-binding capacity and to provide additional bulk without adding caloric value, or a stabilizer comprising at least one gum to provide a desired amount of elasticity and binding in the foodstuff, wherein the mix provides a baked product having consistency and texture equivalent to conventional baked products without the use of gluten.

10. The dietetic food composition of claim 9, wherein said bulking agent comprises a mixture of soluble and insoluble fibers.

11. The dietetic food composition of claim 9, wherein the stabilizer comprises about 0.1 to about 0.5% by weight of said food composition.

12. The dietetic food composition of claim 10, wherein a weight ratio of the stabilizer to the insoluble fiber and an insoluble non-toxic calcium salt is about 0.1:1.0 to about 1.0:1.0.

13. The dietetic food composition of claim 9, wherein particular functional properties comprise water activity reduction, control of starch gelatinization, heat stability, bulking capability and viscosity.

14. The dietetic food composition of claim 9, wherein the low carbohydrate flavoring comprises at least one of a cocoa powder, all nuts, all green vegetables and legumes, chocolate, vanilla, coffee, mocha, carrots, tomatoes, fruits, herbs and any combination thereof.

15. The dietetic food composition of claim 9, wherein the food product comprises at least one of a dairy product, a snack bar, a salad dressing, a candy, a topping and a beverage.

16. The dietetic food composition of claim 9, wherein the low carbohydrate flavoring comprises about 10%–60% by weight of said food composition.

17. A sugar-free baked food product comprising:
   a gluten-free baked good or snack bar including:
   a sugarless natural sweetening agent having particular functional properties of sugar, said sweetening agent consisting essentially of xylitol;
   a whey protein in an amount between about 2 to about 40% by weight to support a structure of the baked food product produced using the food composition; and
   at least one of a bulldng agent to provide water-binding capacity thereby increasing the viscosity of the baked food product to a desired level and to provide additional bulk without adding caloric value, or a stabilizer to provide a desired amount of elasticity and binding to produce said baked food product without adding gluten.

18. The sugar-free baked food product of claim 17, wherein a texture of the baked food product is maintained to resemble a sugar-containing baked food product.

* * * * *